ary Examiner—Lorraine T. Kendell
United States Patent [19]

Holst et al.

[11] 4,186,238

[45] Jan. 29, 1980

[54] HYDROPHILIC ARTICLES OF WATER-INSOLUBLE POLYMERS

[75] Inventors: Arno Holst; Michael Kostrzewa; Helmut Lask, all of Wiesbaden, Fed. Rep. of Germany

[73] Assignee: Hoechst Aktiengesellschaft, Fed. Rep. of Germany

[21] Appl. No.: 838,339

[22] Filed: Sep. 30, 1977

Related U.S. Application Data

[63] Continuation of Ser. No. 681,730, Apr. 29, 1976, abandoned, which is a continuation-in-part of Ser. No. 535,972, Dec. 23, 1974, abandoned.

[30] Foreign Application Priority Data

Dec. 24, 1973 [DE] Fed. Rep. of Germany ....... 2364628

[51] Int. Cl.$^2$ .......................... B32B 5/16; D02G 3/00
[52] U.S. Cl. .................................... 428/326; 428/323; 428/372; 428/393; 428/534; 428/536
[58] Field of Search ............... 428/323, 326, 327, 534, 428/536, 393, 372; 80/116 R, 181; 260/231 A, 17 R, 21 Z, 94.96 A; 536/57, 58, 84, 85

[56] References Cited

U.S. PATENT DOCUMENTS

| | | | |
|---|---|---|---|
| 2,245,499 | 6/1941 | Reichel et al. | 428/536 X |
| 2,339,562 | 1/1944 | Eustis | 428/198 X |
| 2,710,816 | 6/1955 | Evans et al. | 428/393 X |
| 2,796,656 | 6/1957 | Schappel et al. | 428/393 X |
| 2,838,455 | 6/1958 | Tompkins | 428/393 X |
| 2,968,581 | 1/1961 | Kress | 428/536 X |
| 3,252,826 | 5/1966 | Salzinger | 428/536 X |
| 3,259,537 | 7/1966 | Battista | 428/536 X |
| 3,275,580 | 9/1966 | Battista | 428/326 X |
| 3,525,735 | 8/1970 | Miller | 536/85 X |
| 3,589,364 | 6/1971 | Dean et al. | 128/285 X |
| 3,936,441 | 2/1976 | Holst et al. | 260/231 A |
| 3,965,091 | 6/1976 | Holst et al. | 260/231 A |

*Primary Examiner*—Lorraine T. Kendell
*Attorney, Agent, or Firm*—James E. Bryan

[57] ABSTRACT

This invention relates to a hydrophilic shaped article of a water-insoluble polymer selected from the group consisting of regenerated cellulose, cellulose ether, cellulose ester and polyalkylene, and capable of forming fibers and films, said article containing amorphous particles of an originally water-soluble cellulose ether prepared from natural cellulose and rendered by chemical modification at least partly water-insoluble while remaining water-absorbent.

5 Claims, No Drawings

HYDROPHILIC ARTICLES OF WATER-INSOLUBLE POLYMERS

This is a continuation of application Ser. No. 681,730, filed Apr. 29, 1976, now abandoned, in turn, a continuation-in-part of Ser. No. 535,972, filed Dec. 23, 1974, now abandoned.

The invention relates to articles for example fibers, films and spongy products, of polymers of increased hydrophilic character.

It has been proposed to produce articles of regenerated cellulose by introducing a material which bonds to the cellulose, and contains an active component, into the cellulose before the final regeneration of the latter, note U.S. Pat. No. 3,905,954. The character of the active component can be such that, if desired, the hydrophilic character of the regenerated cellulose is greater than it would be without modification with the active component. The structures obtained in accordance with this process are modified throughout their entire mass. Accordingly, their physical properties differ from those of the corresponding unmodified structures, in accordance with the intended result of this process. However, it may result in an undesired lowering of tensile strength, extensibility and flexural strength of resulting structures. More importantly, however, the modifications possible are restricted not only to the manufacture of structures of cellulose or cellulose derivatives but also in the achievable physical effects, for example with regard to the permeability of films manufactured by the process to water and other liquids.

In U.S. Pat. Nos. 3,259,537 and 3,275,580, there is described an article of a mixture of an organic polymer and cellulose crystallite aggregates or derivatives. Those crystallite aggregates have an average level-off D.P. value in the range of from about 15 to about 375 anhydroglucose units and the specific value will be dependent upon the source material, which in all instances has an actual D.P. greater than its average level-off D.P. and was modified by the controlled acid hydrolysis of cellulose to reflect a destruction of the original amorphous structure of the cellulosic source material. The derivatives of cellulose crystallite aggregates possess physical characteristics and properties similar to those of cellulose crystallite aggregates.

The present invention provides articles, which have been rendered hydrophilic, of water-insoluble polymers which can be manufactured from polymeric material other than regenerated cellulose material and can be manufactured with a great range of hydrophilic properties. The present invention provides an article or shaped structure of a polymer capable of forming fibers and films and being water-insoluble, which contains, distributed within its mass or coated on its surface, particles of cellulose ethers that are inherently water-soluble but have been rendered at least partly, preferably more than 50% by weight, water-insoluble by chemical modification, but are still capable of absorbing water.

The structures or articles constructed according to the invention may be shaped by any process suitable for the shaping of the base polymer. A pulverulent or granular material of modified cellulose ether may, for example, be added to the polymer mass before shaping and uniformly distributed therein. Thus, for example the customary precipitation processes are used if filaments, films or sponges of regenerated cellulose are being manufactured, or the casting process is used if films of cellulose acetate are being manufactured, while melt extrusion is used principally if structures of polyethylene or other polyalkylenes or other extrusible polymers are being manufactured. Articles which have the particles as a surface covering are suitably manufactured by sprinkling the supporting article, composed of the polymer, with the particles, if the surface being sprinkled is either provided with an adhesive or is in a state in which the surface itself acts as an adhesive. The polymeric base mass of the articles according to the invention can in principle be composed of any polymer from which self-supporting films, or fibers or filaments, can be manufactured. Further examples of polymers which may be mentioned are water-insoluble alkyl celluloses, such as, for example, aqueous alkali-soluble hydroxyethyl cellulose, methyl cellulose or hydroxypropyl cellulose, polyacrylonitrile, polyamides, polyethylene, polypropylene and polyesters, for example polyethylene terephthalate.

The particles are generally finely pulverulent to granular. Their particle size is in the range of 0.01 to 2 mm and depends upon the end use of the structure. The particles are composed of cellulose ethers, such as for example carboxymethyl cellulose, hydroxyethyl cellulose or methylhydroxyethyl cellulose, which are modified. Examples of possible modifying agents for cross-linking are: dimethylolmethylene-bis-acrylamide; methylene-bis-acrylamide; trichloro-pyrimidine, and tetrachloropyrimidine; cyanuric chloride; epichlorohydrin; dichloroacetic acid, diepoxides or their precursors di-α-halogenohydrins. Such materials are disclosed in U.S. Pat. Nos. 3,589,364, and 3,936,441.

Further examples of possible modifiers are: N-methylolacrylamide; N-(acrylamidomethylene)-acetamide; N-(acrylamidomethylene)-formamide; N-(acrylamidomethylene)-amylurethane; N-(acrylamidomethylene)-methylurethane; N-(acrylamidocarboxymethylene)-ethylurethane; N-(acrylamidomethylene)-methoxyethylurethane and vinyl sulfonamide. Such modified cellulose ethers are described in U.S. patent application Ser. No. 524,822, filed Nov. 18, 1974 now U.S. Pat. No. 3,965,091. The amount of added modified cellulose ether particles can be varied within wide limits depending upon what degree or what type of hydrophilic character, for example of swelling capacity or ion exchange capacity, is desired. However, in general, the maximum amount of additive should be limited such that the mechanical strength of the film or other structure is not significantly reduced. For example, for sodium carboxymethyl cellulose (Na-CMC) which is slightly modified and therefore swells very greatly in water, this maximum is at 50% by weight of the total in a base of regenerated cellulose. In the case of hydroxyethyl cellulose (HEC) of low substitution and cellulose acetate a maximum is reached at about 30 to 40% by weight of the total. The lower concentration limit depends upon the nature and on the action which the particles of modified cellulose ethers are to bring about.

A parameter which also can be varied within wide limits is the degree of modification, for instance of cross-linking of the cellulose ether of which the particles are composed. When using minor amounts of, for instance, cross-linking agents, for example from 3 to 10% by weight of epichlorohydrin, relative to Na-CMC, when producing Na-CMC fibers, highly swellable fibers are obtained. At higher degrees of cross-linking, the swellability of the cellulose ether greatly decreases and its water-insoluble content increases. If, for example, about 33% by weight of these highly swellable Na-CMC fibers (about 20-fold water absorption) are incorporated into a regenerated cellulose film, the swelling factor of the film rises from about 150% (pure regenerated cellulose) to about 350%.

In order to make modified water-insoluble ionic cellulose ethers more readily accessible for ion exchange processes it is sometimes advisable to locate them on the surface of a structure, for example of a film. A regenerated cellulose film of which the surface is covered with the particles is produced, for example, by sprinkling finely ground cross-linked Na-CMC homogeneously through a sieve onto an as yet not regenerated web of viscose and then regenerating the viscose web in the usual manner to form regenerated cellulose. This gives a hydrated cellulose film coated on one side with cross-linked Na-CMC.

The examples which follow further illustrate the invention. Examples 1 to 3 relate to the manufacture of regenerated cellulose films which are modified with particles of Na-CMC modified by cross-linking with epichlorohydrin. Examples 4 and 5 describe the manufacture of films of cellulose acetate and particles of cross-linked Na-CMC. In Example 6, particles of cross-linked Na-CMC are used with films of HEC of a low degree of etherification as the carrier material. This water-insoluble HEC has an average degree of substitution of about 0.2 and gives a clear solution in 5 to 8% by weight sodium hydroxide solution; the alkaline film can be regenerated by adding acid and a clear film is obtained which is rendered cloudy by the heterogeneous cellulose ether additive. Examples 7 to 13 relate to further films of regenerated cellulose (hydrated cellulose) modified with cross-linked cellulose ethers. Examples 14 to 17 relate to the manufacture of films coated on one side with cross-linked cellulose ethers.

The hydrophilic structures according to the invention can be used in many fields of industry. As films, for example, they can be used as ion exchangers or as dialysis membranes or as osmosis membranes. In the form of fibers they serve for the manufacture of textiles of better absorbency for water, which, inter alia, also makes the textiles pleasanter to the human skin, or for the manufacture of leather-like products.

EXAMPLE 1

1 g of finely fibrous water-insoluble cross-linked Na-CMC, which was cross-linked with epichlorohydrin, contained about 25% by weight of soluble constituents and had a water retention capacity of 20 times its weight and a theoretical exchange capacity of about 3.5 milliequivalents/g, was homogeneously incorporated, in a 3 roll mill, into 100 g of spinnable viscose containing about 10% by weight of cellulose. A layer of 0.2 to 0.4 mm thickness of the modified viscose was cast on a glass plate and regenerated in the usual manner. A transparent regenerated cellulose film was obtained, which as a result of the embedded water-insoluble cross-linked Na-CMC fibers had a total theoretical exchange capacity of about 0.32 milliequivalent/g. The water retention capacity of the film was about 250% by weight. A cellulose hydrate film manufactured under the same conditions has a water retention capacity of 125% by weight.

EXAMPLE 2

The expieriment was carried out as in Example 1 but the amount of cross-linked Na-CMC incorporated was increased to 5 g (about 33% by weight of Na-CMC, based on the finished film). Cloudy films with a theoretical exchange capacity of about 1.15 milliequivalents/g were obtained. Their water-retention capacity was about 370% by weight.

EXAMPLE 3

The procedure of the above Example 1 was followed but the amount of cross-linked Na-CMC was increased to 10 g (50% by weight of Na-CMC, based on the finished film). An opaque film visually resembling a paper fleece was obtained. The individual fibers were held together by the regenerated cellulose binder. The theoretical exchange capacity was about 1.7 milliequivalents/g. The water retention capacity was about 390% by weight.

Since the cross-linked Na-CMC withdraws water from the viscose, the mixture became difficult to homogenize if Example 1 was carried out with more than 10 g of cross-linked Na-CMC. On the other hand, though water or sodium hydroxide solution could be added without difficulty to the viscose, there was then a loss in the strength of the resulting film.

EXAMPLE 4

10 g of slightly cross-linked fibrous Na-CMC were stirred homogeneously into a 15% by weight cellulose acetate solution in acetone so as to give a ratio of cellulose acetate to cross-linked cellulose ether of 1:1. A 0.5 mm thick layer was cast and the solvent was evaporated off. In the resulting film, the fibers of cross-linked Na-CMC fibers were embedded in a transparent layer of cellulose acetate so that the film was opaque white. The theoretical exchange capacity of the film was about 1.7 milliequivalents/g. Its water retention capacity was about 350% by weight. The water retention capacity of a cellulose acetate film, in contrast, is only 20% by weight.

EXAMPLE 5

The procedure followed was as in Example 4, but the amount of cross-linked Na-CMC was reduced to half and, after casting, the layer precipitation was carried out with water. An opaque white membrane was obtained, which had a theoretical exchange capacity of 1.15 milliequivalents/g. Its water retention capacity was about 360% by weight.

EXAMPLE 6

The procedure followed was as in Example 2, but HEC of low degree of etherification, with an average degree of substitution of about 0.2, was employed as the polymeric film material. 5 g of cross-linked Na-CMC were incorporated homogeneously into 100 g of a 10% by weight solution of the HEC in 8% aqueous NaOH and a film was obtained by precipitating the 0.5 mm thick web in dilute sulfuric acid. A transparent film having a theoretical exchange capacity of 1.15 milliequivalents/g and a water retention capacity of about 150% by weight was obtained.

EXAMPLES 7 to 13

Table 1 summarizes the essential data of Examples 1 to 6 and their results, and gives those of a further 7 examples (Examples 7 to 13), in which films of regenerated cellulose (hydrated cellulose) which were modified with cross-linked sodium carboxymethyl cellulose and sodium carboxymethylhydroxyethyl cellulose (Na- CMHEC), employing various cross-linking agents, were manufactured as the polymeric carrier material.

Table 1

Cross-linked cellulose ethers incorporated into cellulose-based films

| Example No. | Polymeric carrier material | Cross-linked cellulose ether | Cross-linking agent | Cross-linked cellulose ether, % by weight based on film | Theoretical ion exchange capacity, milliequivalent/g per film | Water retentioon capacity of the film, % by weight |
| --- | --- | --- | --- | --- | --- | --- |
| 1 | Hydrated cellulose | Na-CMC | Epichlorohydrin | 10 | 0.35 | 250 |
| 2 | " | " | " | 33 | 1.15 | 370 |
| 3 | " | " | " | 50 | 1.7 | 390 |
| 4 | Cellulose acetate | " | " | 50 | 1.7 | 350 |
| 5 | " | " | " | 33 | 1.15 | 360 |
| 6 | Hydroxyethyl cellulose | " | " | 33 | 1.15 | 150 |
| 7 | Hydrated cellulose | " | Cyanuric chloride | 33 | 1.15 | 450 |
| 8 | " | " | Dichloroacetic acid | 33 | 1.15 | 308 |
| 9 | " | " | Dimethylolmethylene-bis-acrylamide | 33 | 0.75 | 240 |
| 10 | " | " | Trichloropyrimidine | 33 | 0.70 | 200 |
| 11 | " | " | Tetrachloropyrimidine | 33 | 0.85 | 240 |
| 12 | " | Na-CMHEC | Methylene-bis-acrylamide | 33 | 0.51 | 220 |
| 13 | " | Na-CMC | " | 33 | 0.94 | 280 |

EXAMPLE 14

An 0.5 mm thick layer of viscose ripened for spinning (as in the above Example 1) was cast onto a glass plate. Thereafter, finely ground dry Na-CMC cross-linked with epichlorohydrin was homogeneously sprinkled over the surface through a sieve of appropriate mesh width. The layer was regenerated in the usual manner. The film thus obtained was freed from loosely adhering Na-CMC by washing with water and plasticized by immersion in a glycerin-water mixture. A translucent film was obtained, which is composed of regenerated cellulose coated on one side with fragments of water-insoluble cross-linked Na-CMC fibers. The firmly adhering Na-CMC fibers are freely accessible for ion exchange processes. The theoretical capacity was determined to be about 93.5 milliequivalents/square meter or 1.1 milliequivalents/g of film, by measuring the difference (in the weight per square meter) compared to pure regenerated cellulose. The water retention capacity of the film was about 440% by weight.

EXAMPLE 15

A film was cast as in the above Example 4 from a 15% by weight solution of cellulose acetate in acetone, but before evaporation of the solvent cross-linked Na-CMC was homogeneously sprinkled on the film. A transparent film having a theoretical ion exchange capacity of about 0.9 milliequivalents/g and a water retention capacity of about 33% by weight was obtained.

EXAMPLE 16

An 0.5 mm thick layer was cast as in the above Example 6 from an alkaline HEC solution, cross-linked Na-CMC was homogeneously sprinkled on the surface of the layer as in the above Example 14, and a film was precipitated and washed. A film having a theoretical exchange capacity of about 1.0 milliequivalent/g of film and a water retention capacity of about 130% by weight was obtained.

EXAMPLE 17

The procedure followed was as in the above Example 14 but a Na-CMC cross-linked with cyanuric chloride (instead of with epichlorohydrin) was sprinkled onto the cast viscose layer. The resulting film had a theoretical ion exchange capacity of 1.2 milliequivalents per g of film and a water retention capacity of 280% by weight.

Table 2 summarizes the essential data of Examples 14 to 17, and their results.

Table 2

Cross-linked cellulose ethers, sprinkled onto the surface of cellulose-based films

| Ex. No. | Polymeric carrier material | Cross-linked cellulose ether | Cross-linking agent | Theoretical ion exchange capacity, milliequivalents per g of film | Water retention capacity of the film, % by weight |
| --- | --- | --- | --- | --- | --- |
| 14 | Hydrated cellulose | Na-CMC | Epichlorohydrin | 1.1 | 440 |
| 15 | Cellulose acetate | Na-CMC | " | 0.9 | 33 |
| 16 | Hydroxyethylcellulose | Na-CMC | " | 1.0 | 130 |
| 17 | Hydrated cellulose | Na-CMC | Cyanuric chloride | 1.2 | 280 |

EXAMPLE 18

30% by weight of a dry sodium carboxymethyl cellulose cross-linked with 50% by weight of epichlorohydrin were homogeneously mixed into finely ground high pressure polyethylene powder. The homogeneous mixture was granulated by chopping a strand extruded on a twin screw extruder heated to 165° C., so that chips, of diameter and height about 3 to 4 mm, of polyethylene modified with the cross-linked Na-CMC were produced. The chips were fibrillated to fibers by means of a cutting mill. The fibrous samples showed a water retention capacity of about 26% and a measurable ion exchange capacity of about 0.78 milliequivalent/g.

The starting polyethylene had virtually no water retention capacity, the value being 2%.

EXAMPLE 19

To show the difference between modified cellulose ethers made from natural cellulose and those made from cellulose crystallite aggregates in any case, 100 g of cellulose crystallite aggregates in 300 g of 87% isopropanol were alkalized with 46 g of aqueous NaOH solution (50%) by kneading them for 45 minutes at 20° C. Then, the mixture was etherified by adding 55 g of sodium monochloracetate and kneading it for another hour at 70° C. Then it was cross-linked with 50 g of aqueous dimethylol-methylene-bisacrylamide solution (30%) while it was kneaded for one hour at 50° C. Then it was neutralized with acetic acid, washed salt-free with 80% methanol, and dried. The following table 3 shows two of the physical/chemical properties of the product in each case:

Table 3

| Source material | Capacity of retaining water, in g of water per 100 g of modified cellulose ether | Water-soluble portion, in percent by weight |
|---|---|---|
| natural cellulose | 2895 | 21 |
| cellulose crystallite aggregates | unmeasurably low | 78 |

It will be obvious to those skilled in the art that many modifications may be made within the scope of the present invention without departing from the spirit thereof, and the invention includes all such modifications.

What is claimed is:

1. A hydrophilic shaped article in the form of a fiber, a filament, a film or a spongy product consisting essentially of (a) a water-insoluble polymer selected from the group consisting of regenerated cellulose, cellulose ether, cellulose ester, and polyalkylene and capable of forming fibers and films and (b) of from an amount effective to render said article hydrophilic up to 50% by weight of the total weight of the article, of amorphous particles of a size within the range of about 0.01 to 2 mm of an originally water-soluble cellulose ether selected from the group consisting of carboxymethyl cellulose, hydroxyethyl cellulose and methylhydroxyethyl cellulose, prepared from natural cellulose and rendered by chemical modification with a cross-linking agent more than 50% by weight water-insoluble while remaining water-absorbent, said cross-linking agent being selected from the group consisting of dimethylolmethylene bisacrylamide, methylene-bis-acrylamide, tri- and tetrachloropyrimidine, cyanuric chloride, epichlorohydrin, dichloracetic acid, a diepoxide and a di-α-halogenohydrin.

2. An article as claimed in claim 1, the particles of which are on the surface of the article only.

3. An article as claimed in claim 1 which is a fiber.

4. An article as claimed in claim 1 which is a filament.

5. An article as claimed in claim 1 which is a film.

* * * * *